(12) United States Patent
Mott et al.

(10) Patent No.: US 7,614,554 B2
(45) Date of Patent: Nov. 10, 2009

(54) ELECTROSURGICAL DEVICE HAVING RFID AND OPTICAL IMAGING CAPABILITIES

(75) Inventors: Peter Earl Mott, Baldwinsville, NY (US); David Miller, Brewerton, NY (US); Wie Lee, Manlius, NY (US); Brian Paul Ford, Cicero, NY (US)

(73) Assignee: JADAK Technologies, Inc., Liverpool, NY (US)

( * ) Notice: Subject to any disclaimer, the term of this patent is extended or adjusted under 35 U.S.C. 154(b) by 382 days.

(21) Appl. No.: 11/420,350

(22) Filed: May 25, 2006

(65) Prior Publication Data

US 2007/0210159 A1 Sep. 13, 2007

Related U.S. Application Data

(63) Continuation-in-part of application No. 11/308,170, filed on Mar. 9, 2006.

(51) Int. Cl.
*G06K 7/14* (2006.01)
(52) U.S. Cl. .................. 235/440; 235/454
(58) Field of Classification Search ............ 235/454, 235/440, 455, 472.01, 472.02, 472.03
See application file for complete search history.

(56) References Cited

U.S. PATENT DOCUMENTS 5,479,359 A * 12/1995 Rogero et al. .............. 702/24
2004/0118920 A1* 6/2004 He ............................ 235/454

* cited by examiner

*Primary Examiner*—Thien M Le
(74) *Attorney, Agent, or Firm*—David L. Nocilly; Bond Schoeneck & King, PLLC

(57) ABSTRACT

A medical device, such as an electrosurgical scalpel, having a base unit and one or more attachable implements for performing medical procedures. The device include a host controllable module for capturing images of the attachable implement, decoding information contained in the image, and reporting the results of the decoding to the medical device. The host controllable module includes a system microcontroller that interconnects an optical imager and/or an RFID transceiver through the single interface to the host medical device. As a result, the module may be easily retrofit into existing medical devices and programmed to perform operations on legacy instruments as well as additional functions not previously available to the medical device.

19 Claims, 11 Drawing Sheets

ELECTROSURGICAL DEVICE HAVING RFID AND OPTICAL IMAGING CAPABILITIES

CROSS-REFERENCE TO RELATED APPLICATIONS

The present application is a continuation-in-part of application Ser. No. 11/308,170, filed on Mar. 9, 2006.

FIELD OF INVENTION

The present invention relates to data collection systems and, more specifically, to a system and method for integrating host controllable radio frequency identification and optical imaging into a medical device.

DESCRIPTION OF PRIOR ART

Technologies such as barcode imaging and radio frequency identification (RFID) can play an important role in various fields by automating processes and improving safety and security. Barcodes are essentially graphic representation of data (alpha, numeric, or both) that is machine-readable. Barcodes encode numbers and letters into different types of symbologies, such as linear codes, two-dimensional codes, and composite codes (a combination of linear and two-dimensional codes). In more recent applications, referred to as digital or optical image capture, an optical device snaps a digital picture of the barcode and software in the imager orients the picture and decodes the barcode(s) contained in the picture. RFID is a wireless communication technology that utilizes radiowaves for automatic identification and data capture of information for the purpose of identifying and tracking objects, people, or even animals. Signals in the radio frequency (RF) range of the electromagnetic spectrum are used to communicate data between a two transceiver devices. An RFID system typically consists of the three main components: a tag, a reader, and the software/firmware for controlling the system. Tags are placed on objects, people or animals and directly or indirectly contain information about the object, person or animal. The reader uses RF energy to interrogate the tag and read the information it contains, or even write data to the tag.

The ability to more accurately track objects and instantly provide data about the object is becoming a particularly important tool in the medical field, where automated systems can help improve safety procedures and limit human errors. In one such system, medical samples and prescription medication may often be provided with a barcode to assist with tracking the formulation and delivery of the medication or samples, and proper identification of the patient to whom the medication or samples belong. RFID technology may be used for tracking medical devices to ensure that the right device is available to the correct patient at the correct time, servicing and administering drugs, or to track the location of high-risk devices like implants that may relocate within a patient.

Bar code identification systems and RFID systems generally require middleware applications that provide an interface between the readers and the host device or computer. The middleware filters and structures the data read from the tags and integrates it into the host application, which stores the information from the tag or dictates the action to be taken with the information. Middleware and host data management software applications are usually provided by an RFID vendor or by third party applications developers. These systems are not, however, capable of combining the advantages of machine vision and RFID into a modular package that may be easily integrated into existing medical devices or adapted for use in new systems and easily controlled by the user. Instead, they require the integration of multiple systems and the use of sophisticated processing software to accomplish any functions beyond rudimentary barcode identification and RFID interrogation.

In addition, conventional systems for utilizing barcodes and RFID in the medical field are often rudimentary. For example, medical instruments such as electrosurgical scalpels have one or more reusable or disposable medical implements (i.e., scalpels) that may be attached to a base unit. Safe operation of the scalpel requires that the proper implement is attached to the base unit, and the base unit is configured for the safe operation of the particular instrument. A conventional identification method for such systems comprises the addition of distinctive markings to the implement which are recognized by photodiodes interfaced with or included as part of the base unit. While these systems provide basic identification capabilities, they lack sophisticated processing capabilities, provide only rudimentary information to the host unit, may not be easily upgraded in the field, are not secure (e.g., wrong instrument for wrong application), cannot distinguish between inferior "knock-off" implements that may be unintentionally intentionally attached to the base unit (e.g., wrong manufacturer), and do not always effectively distinguish between similar implements.

SUMMARY OF THE INVENTION

It is a principal object and advantage of the present invention to provide host controllable RFID and optical imaging capabilities to a medical device.

It is an additional object and advantage of the present invention to provide a modular RFID and optical imaging system that may easily retrofit into legacy medial devices.

It is a further object and advantage of the present invention to provide a medical device having RFID and optical imaging capabilities that is field programmable.

Other objects and advantages of the present invention will in part be obvious, and in part appear hereinafter.

In accordance with the foregoing objects and advantages, the present invention comprises a medical device, such as an electrosurgical scalpel, having a host microcontroller that is interfaced to a module having optical imaging and/or an RFID reading capabilities. The optical image and RFID module is operated by a single host controllable microcontroller that is programmed to respond to host commands sent by the microcontroller of the medical device, and programmed to return data obtained from one or more objects by the optical imager and RFID reader back to the medical device. The microprocessor of the optical imager and RFID reader is configurable via the host interface to selectively provide RFID reading or writing, optical imaging, barcode reading, or a variety of combinations of both techniques. The module is further programmed to allow the host medical device to trigger the RFID reader and optical imager. Additionally, the module can auto-trigger, i.e., it can automatically trigger and read upon insertion of a device without prompting from the host. Accordingly, the functionality delivered by the module is possible in the medical device while maintaining a single connection to the host computer. The present invention may be easily retrofit into a pre-existing medical device having a only a single communication port and then be programmed to perform a variety RFID and optical imaging tasks previously unavailable to the medical device, or easily integrated into a new medical device without the need for additional hardware or complicated software for performing image and interrogation data processing.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
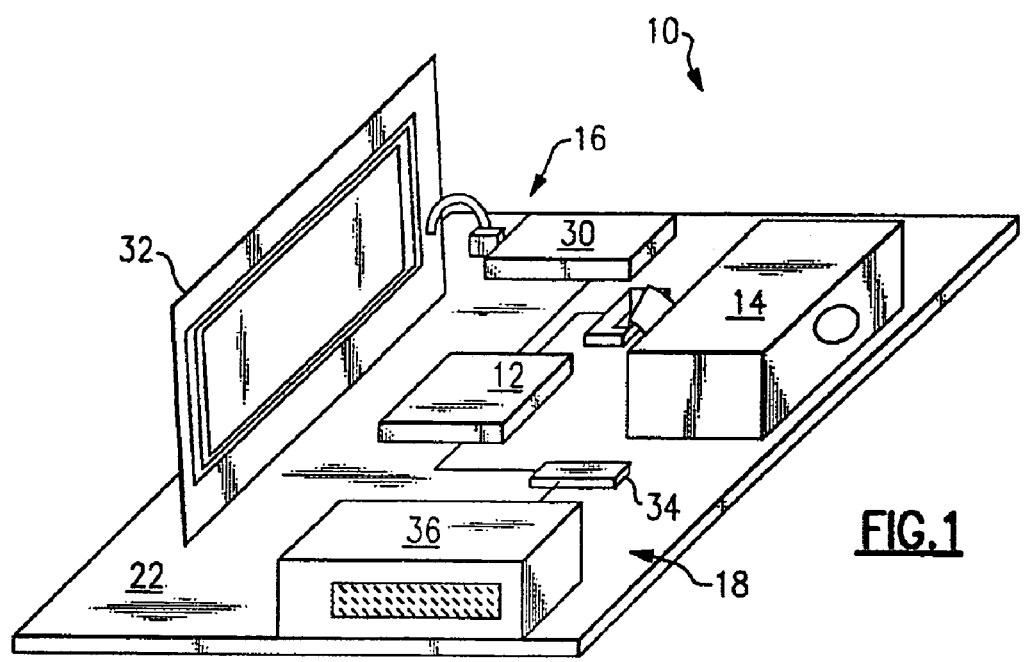
FIG. 1 is a perspective view of a combined RFID and optical imager according to the present invention.

Referring now to the drawings, wherein like numerals refer to like parts throughout, the present invention comprises an electrosurgical scalpel including RFID and/or optical imaging capabilities. RFID and optical imaging capabilities are preferably provided via a combined RFID and optical imaging module 10 that is easily interfaced with the electrosurgical scalpel, or retrofit into an existing scalpel, through a single interface to provide host controllable and field programmable RFID interrogation and/or optical imaging capabilities.

There is seen in FIG. 1 a combined RFID and optical image module 10 according to the present invention that may be used in connection with a medical device such as an electrosurgical scalpel. Module 10 generally comprises a microcontroller 12 that interconnects a first submodule, such as an optical imager 14 and, optionally, a second submodule, such as a RFID unit 16, to a single host interface 18. Alternatively, module 10 is capable of interconnecting any variety of data capturing devices as submodules and providing host controllability, including additional optical imagers or RFID transceivers, lasers, scales, thermometers or temperature probes, etc., in any variety of combinations thereof. Module 10 may be arranged on a single printed circuit board 22 and encased as a single unit or housing. Integration of imager 14 and RFID unit 16 through interface 18 allows for combining control of operation of both submodules, such as RFID reading and barcode, through module 10, as will be explained in detail hereinafter.

Figure 2:
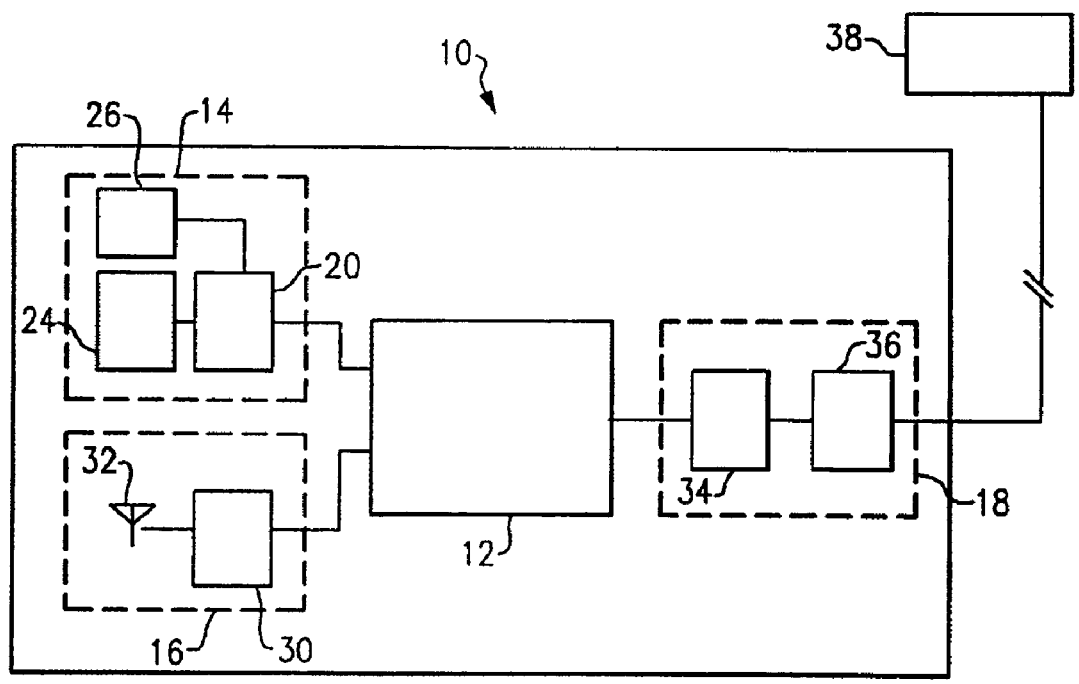
FIG. 2 is a schematic of a combined RFID and optical imager according to the present invention.

Referring to FIG. 2, a first submodule of module 10 is illustrated as an optical imager 14 comprising an image engine 20 having image processing circuitry interconnected to microcontroller 12 for omni-directional optical scanning. Image engine 20 controls an image sensor 24, such as a complementary metal oxide semiconductor (CMOS) image sensor, and is capable of capturing two-dimensional images of 1D linear barcodes, 2D stacked/matrix barcodes, standard optical character recognition (OCR) fonts, Reduced Space Symbology (RSS) barcodes, and postal barcodes, as well as providing image captured images for use in a wide range of applications, such as image and shape recognition, signature capture, image capture, and non-standard optical character recognition. Imager 14 may further include an integrated illumination source 26 connected to engine 20, such as one or more light emitting diodes (LEDs) of various wavelengths, to enhance illumination, operation, and image capture. For example, module 10 may include red LEDs for general illumination and green LEDs for targeting. Imager 14 may comprise, but is not limited to, an IT4X10/80 SR/SF or IT5X10/80 series imager available from Hand Held Products, Inc. of Skaneateles Falls, N.Y. that is capable of scanning and decoding most standard barcodes including linear, stacked linear, matrix, OCR, and postal codes. Specifically, the IT5X10/80 series imager is a CMOS-based decoded output engines that can read 2D codes, and has image capture capabilities sufficient for use with module 10.

Imager 14 obtains an optical image of the field of view and, using preprogrammed algorithms in image engine 20, deciphers the context of the image to determine the presence of any decodable barcodes, linear codes, matrix codes, and the like. Image engine 20 may be programmed to perform other image processing algorithms on the image captured by imager 14, such as shape recognition, match filtering, statistical analysis (e.g., threshold detection), and other high-level processing techniques. Alternatively, a captured image may be processed by microprocessor 12, albeit with a decreased level of performance due to the additional communication time needed to transfer images from image engine 20 to microprocessor 12.

Second submodule of module 10 may comprise an RFID unit 16 including a RFID transceiver 30 and associated RFID antenna 32 supporting standard RFID protocols, such as the TI Tag-it transponder protocol or ISO 15693. For these protocols, transceiver 30 operates at 13.56 MHz, and may comprise a S6700 Multi-Protocol Transceiver IC available from Texas Instruments of Dallas, Tex. Depending on the application, other frequency transceivers may be more appropriate based on target range, power availability, cost, etc. RFID unit 16 may further include a speaker or LED (not shown) for audibly indicating a successful interrogation of a RFID tag.

Antenna 32 is preferably a loop antenna of various sizes and turns implemented on a printed circuit board and connected to module 10, or a wire loop installed antenna installed directly onto module 10. Antenna 32 may be positioned remotely, thereby reducing the footprint of module 10 using an external connector, such as a MMCX coaxial connector. RFID transceiver 30 may be programmed to interrogate passive or active tags, process signals received from such tags (e.g., analog to digital conversion), and provide the information from the tags to microcontroller 12 for further processing or transmittal to a host computer via interface 18.

Host interface 18 comprises a host transceiver 34 and a host connector 36 for interconnection to a host device 38. Interface 18 may comprise a conventional RS232 transceiver and associated 12 pin RJ style jack. For example, an ADM202EARN available from Analog Devices, Inc. of Norwood, Mass. is a suitable RS-232/V.28 interface device having compliant levels of electromagnetic emissions and immunity. Alternatively, interface 18 may comprise other conventional buses, such as USB, IEEE 1394, I2C, SPI, or PCMCIA, or other connector styles, such as an FFC style to an embedded host or another module 10. Interface 18 may also comprise a wireless transceiver in lieu of connector 36 for wireless communication to a host computer. A Stewart Connector Systems Inc. SS-641010S-A-NF may serve as connector 36 for mating with a Stewart Connector 937-SP-361010-031 matching connector of a host device. Host interface 18 may also comprise a Molex MX52588 connector. Regardless of the type of connector 36 used, host transceiver 34 is programmed with the applicable protocols for interfacing with a host computer, such as USB, Bluetooth®, and IrDA protocols. Transceiver 34 may also be programmed to support both non-inverted signal sense and inverted signal sense.

Microcontroller 12 comprises a conventional programmable microprocessor having on-chip peripherals, such as central processing unit, Flash EEPROM, RAM, asynchronous serial communications interface modules, serial peripheral interfaces, Inter-IC Buses, timer modules, pulse modulators with fault protection modules, pulse width modulators, analog-to-digital converters, and digital-to-analog converters. Additionally, the inclusion of a PLL circuit allows power consumption and performance to be adjusted to suit operational requirements. In addition to the I/O ports dedicated I/O port bits may be provided. Microcontroller 12 may further include an on-chip bandgap based voltage regulator that generates an internal digital supply voltage from an external supply range. Microcontroller 12 preferably comprises a Motorola MC9S12E128.

The functional integration of imager 14 and RFID unit 16 to interface 18 is accomplished by microcontroller 12, which receives and interprets host commands, and then executes the appropriate functions by driving imager 14 and/or RFID unit 16 accordingly. For example, the operation of imager 14 and RFID unit 16 may be triggered by commands sent to module 10 from a host device 38, or by a hardware button communicating directly with connector 36 or through host device 38. Microcontroller 12 may further be programmed to execute the functions otherwise performed by one or more of image engine 20, RFID transceiver 30, and host transceiver 34, thereby reducing the amount of circuitry and hardware required by module 10.

When integrating imager 14 and RFID unit 16, module 10 has three principle operational modes: image scanning using imager 14, tag interrogation using RFID unit 16, an interleaved mode that is a combination thereof, and a simultaneous mode. In imaging-only mode, module 10 will capture images and perform the applicable algorithms, such as barcode deciphering, until a barcode is detected or the device is un-triggered. In RFID-only, module 10 will interrogate until a tag is successfully read or module 10 is un-triggered. In interleaved mode, module 10 toggles between imaging and interrogation according to a predetermined timeout schedule. In simultaneous mode, module 10 causes simultaneous imaging and interrogation. In addition, module 10 may be programmed with timeouts to prevent hang-ups. As module 10 can receive, interpret, and execute host commands, these modes may be controlled by a user from host device 38.

Microcontroller 12 may direct RFID interrogation using RFID unit 16 in at least two modes. RFID unit 16 may operate in a free form mode that reads and writes data as a continuous stream, which is limited only by memory capacity. Once RFID unit 16 is triggered, depending on the mode, data is transmitted from the serial port. Second, RFID unit 16 may operate in block mode, where a user may access individual blocks of information via commands sent through interface 18 and Interpreted by microcontroller 12.

External control of module 10 is accomplished by a predefined protocol and set of serial host commands that are sent to module 10 from host device 38. The host commands are received by microcontroller 12, which executes the appropriate steps based on the content of the host command. For example, microcontroller 12 may be programmed to recognize host commands that trigger the activation of imager 14 and/or RFID unit 16. Host commands may also be defined to whether the data obtained from imager 14 and/or RFID unit 16 is stored locally in module 10 or passed through interface 18 to host device 38. Host commands may also be provided that enable the various scanning or imaging modes available from imager 14 and RFID unit 16, control the amount of time that imager 14 and RFID unit 16 will attempt scanning before timing out, direct the reading and writing of image and scan data, and select the location where the data is to be written. With regard to imager 14 and RFID unit 16, commands for opening and closing connections to image engine 20 and RFID transceiver 30, as well as commands that return the status of the connection are useful. For example, a host command received from host device 38 may trigger the capture of barcode or RFID data from imager 14 or RFID unit 16. When the scan is complete, a timeout occurs or triggering is turned off via a second host command, and the appropriate feedback is provided to host device 38. The host commands may be preprogrammed into microprocessor 12 and separately provided to host device 38 as a software package for controlling module 10. In addition, software for editing host commands may be supplied to host device 38 to allow a user to edit, add, or delete commands and the corresponding functionality.

Figure 3:
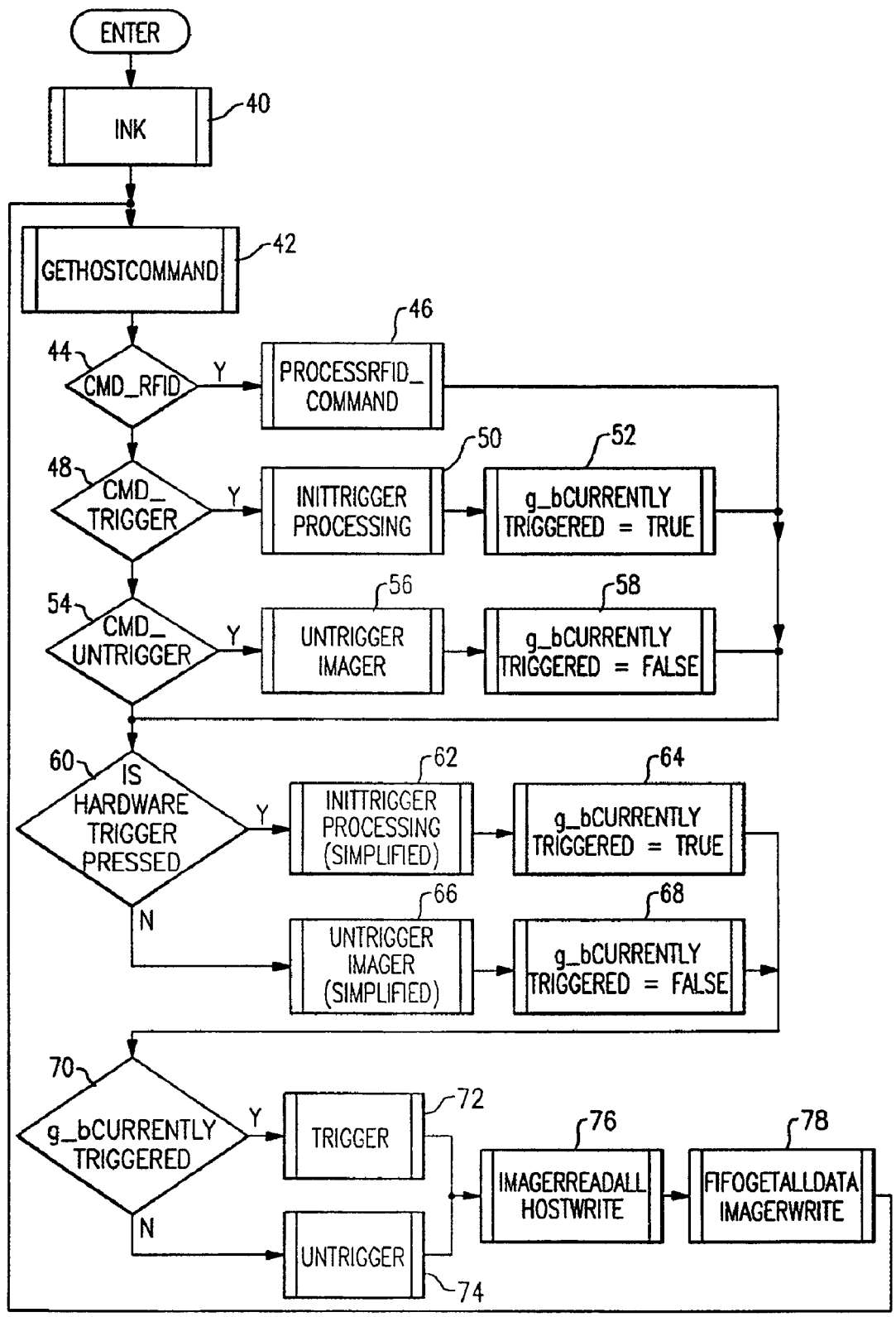
FIG. 3 is a flowchart of main-line processing according to the present invention.

FIG. 3 illustrates an embodiment of main-line host command processing in microprocessor 12 according to the present invention. The specific nomenclature used to define the various routines may be varied by the user or software developer provided that the appropriate functions are performed, and any number of routines and subroutines may be defined and executed in various orders to accomplish image and RFID reading and processing according to the present invention. After initialization 40, microcontroller 12 runs a routine, referred to as GetHostCommand 42, to check whether a host command has been received from host device 38. Upon receipt of a host command, microprocessor 12 checks whether the command is an RFID control command, CMD_RFID 44. If so, the command is processed by routine ProcessRFID_Command 46. If not, a check is performed to see whether the command is a trigger command, CMD_TRIGGER 48. If the command is a trigger command, the appropriate instruction are processed to initiate triggering, InitTriggerProcessing 50 and a variable, referred to as CurrentlyTriggered 52, is assigned the value of TRUE. If the command is not a trigger command, a check is performed to see whether the command is an untrigger command, CMD_UNTRIGGER 54. If the command is an untrigger command, the appropriate steps are taken to stop triggering, UnTriggerImager 56, and a variable, CurrentlyTriggered 58, is assigned the value FALSE.

After any of the above processing, microprocessor 12 checks to see whether a hardware trigger has been pressed 60, the triggering processing is performed, InitTriggerProcessing 62, and a variable, referred to as CurrentlyTriggered 64, is assigned the value of TRUE or FALSE depending on whether the selected device has already been triggered. If a hardware trigger has not been pressed 60, the appropriate instruction are processed to stop triggering, UnTriggerImager 66, and a variable, referred to as CurrentlyTriggered 68, is assigned the value of TRUE or FALSE depending on whether the selected device has already been triggered. Finally, microprocessor checks to see whether the CurrentlyTriggered variable is TRUE or FALSE 70, and then calls function Trigger 72 or function UnTrigger 74 as appropriate. Data is then read from imager 14 and written to the host, ImagerReadAllHostWrite 76, and host data that should be routed to imager 14 is written to it, FifoGetAllDataImagerWrite 78.

Figure 4A:
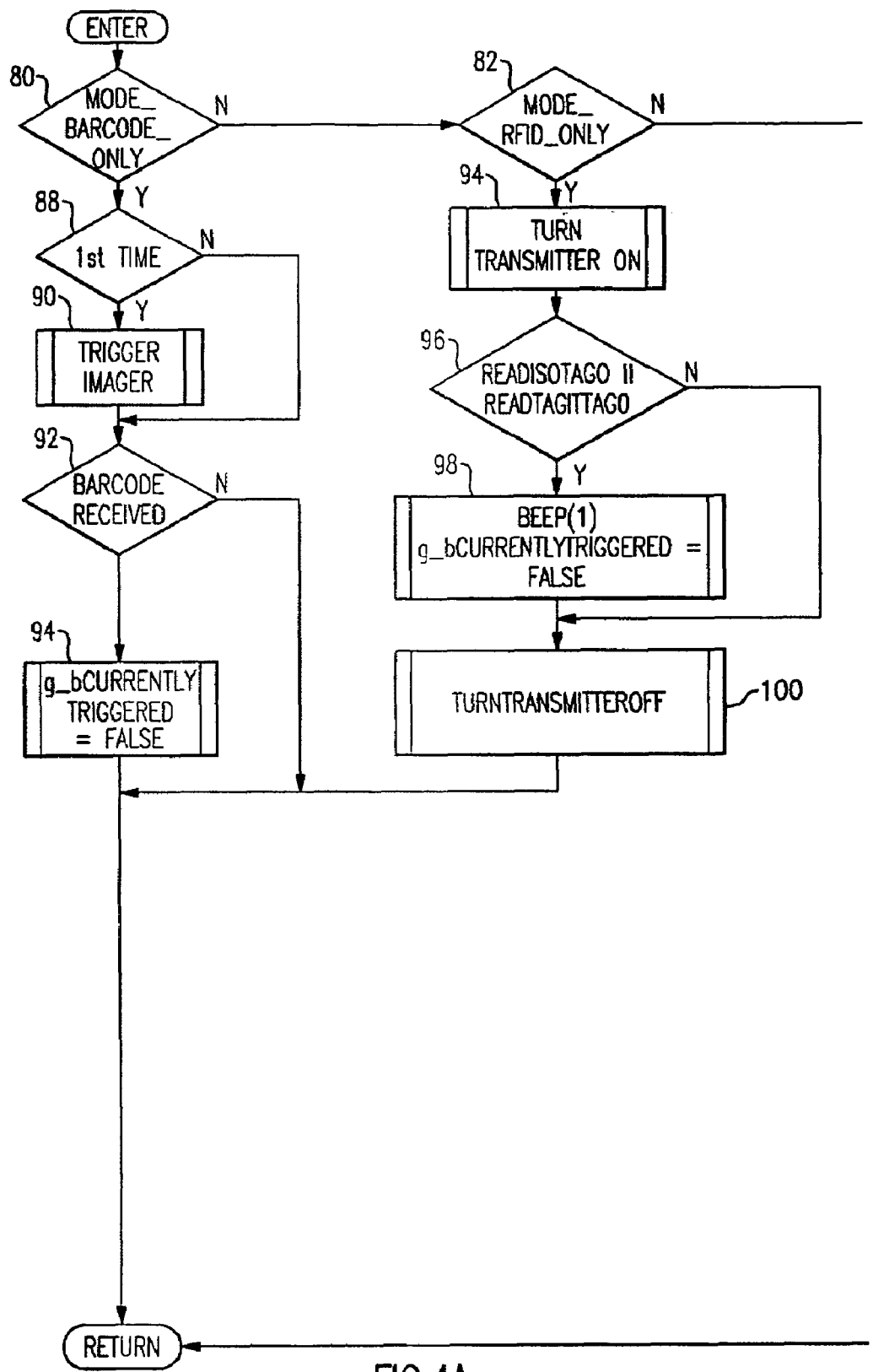
FIG. 4A and FIG. 4B are flowcharts of trigger command processing according to the present invention.
Figure 4B:
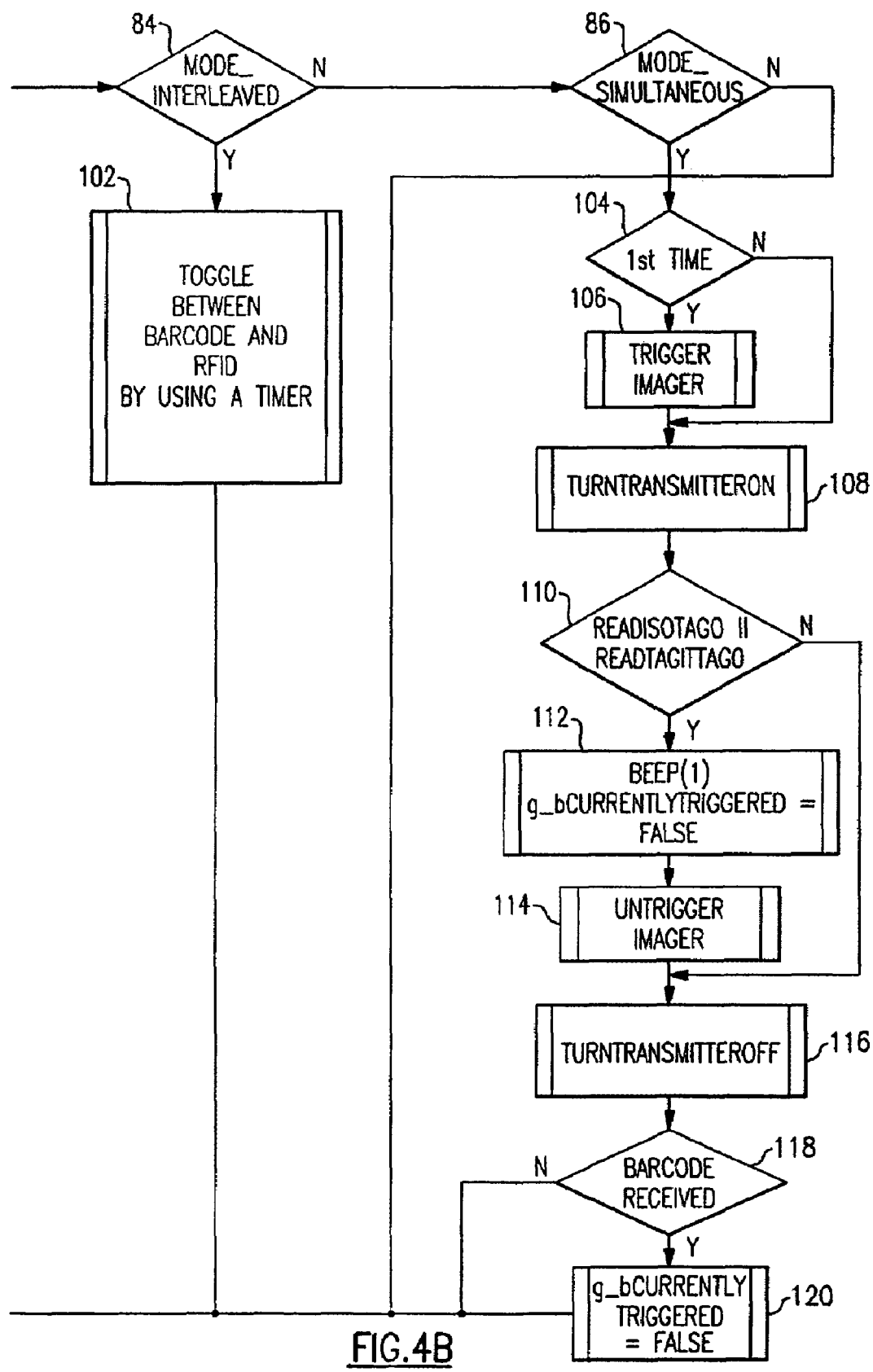

There is seen in FIGS. 4A and 4B, trigger host command processing in microprocessor 12 according to the present invention. Upon receipt of a trigger command, microcontroller 12 first checks to see whether barcode only scanning 80, RFID only scanning 82, interleaved RFID and barcode scanning 84, or simultaneous RFID and image scanning 86 has been previously selected. If bar code only scanning 80 has been selected for the first time 88, and since InitTriggerProcessing 50 has been called, microcontroller 12 triggers imaging 90. If an image is successfully captured and applicable information successfully extracted from the image 92, such as barcode, microcontroller 12 assigns FALSE to the variable CurrentlyTriggered 94. If RFID only scanning 82 has been selected, microcontroller 12 turns the RFID transmitter on 94. If an RFID tag is successfully read 96, an audible tone is sounded and microcontroller 12 sets variable CurrentlyTriggered to FALSE 98. Microcontroller 12 turns transmitter off 100. If interleaved RFID and barcode scanning 84 has been selected, microcontroller 12 toggles operation of imager 14 and RFID unit 16 using a timer 102. If simultaneous RFID and image scanning 86 has been selected, microcontroller 12 checks to see whether the triggering is for the first time 104 and, if so, triggers the imager 106. Transmission from the RFID unit 16 is also turned on 108, and a nearby RFID tag is read 110. If the reading of tag 110 is successful, an audible tone is optionally sounded and variable CurrentlyTriggered is set to FALSE 112. Imager 14 is also untriggered 114 and the transmitter is turned off 116. If the image is successfully processed, e.g., a barcode is received 118, and variable CurrentlyTriggered is set to FALSE 120.

Figure 5:
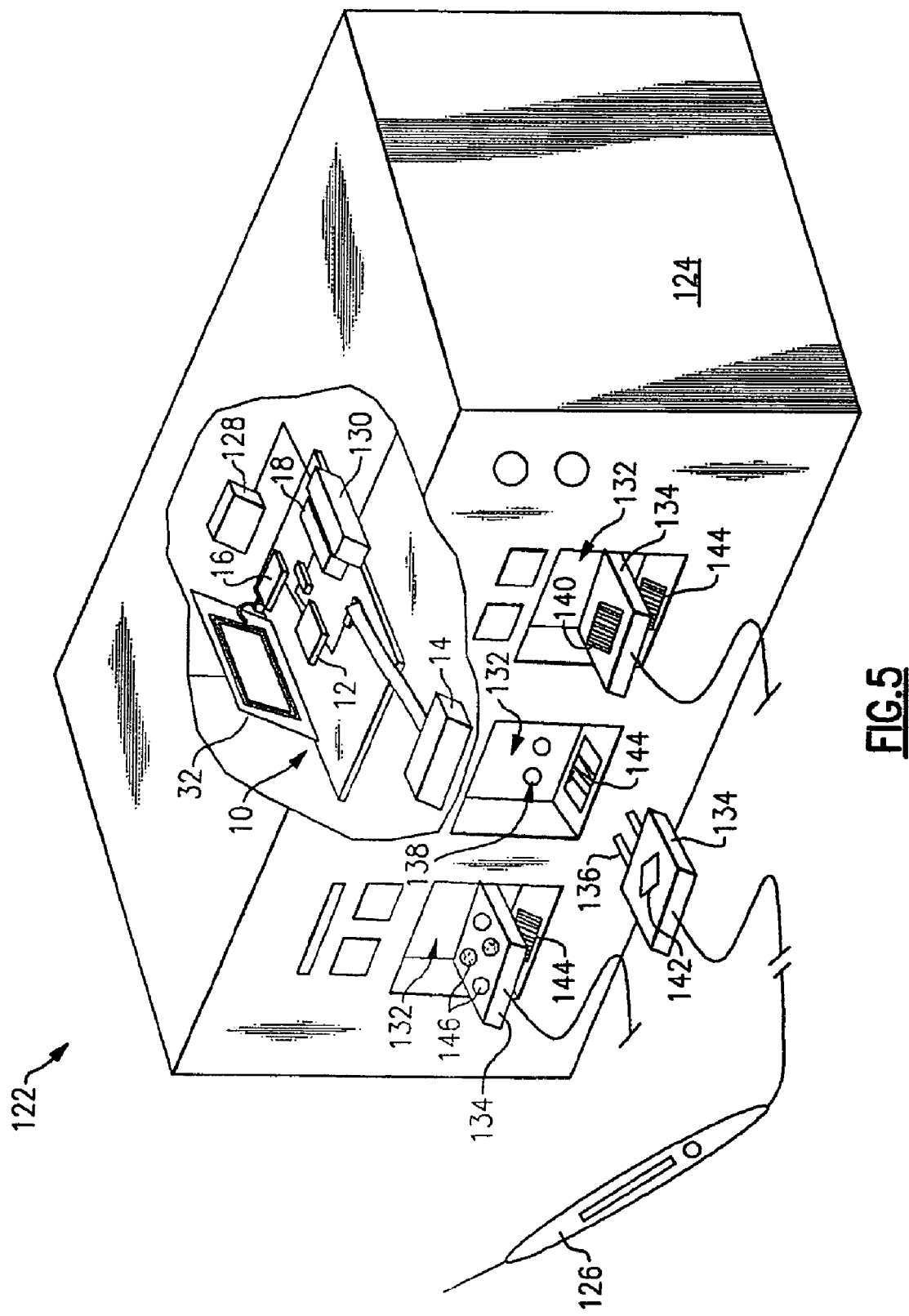
FIG. 5 is a partial cutaway perspective view of a medical device including optical imaging and RFID capabilities according to the present invention

As seen in FIG. 5, another embodiment of the present invention comprises the inclusion of module 10 as part of a medical instrument 122, such as an electrosurgical scalpel having a generator and attachable accessories for delivering the appropriate electrical energy to a patient. Medical instrument 122 thus generally comprises a base unit 124, a patient implement 126 that is connected to or disconnected from base unit 124, and a base microcontroller 128 for controlling the operation of medical instrument 122. Base microcontroller 128 is interconnected to module 10 via a connector 130 that mates with interface 18 of module 10.

Base unit 124 defines one or more receptacles 132 for interconnecting to a plug 134 that is interconnected to one end of implement 126. Each plug 134 is provided with a one or more prongs 136 that are received by corresponding sockets 138 within receptacle 132. Plugs 134 include one or more indicia 140, such as a barcode 140 or a symbol 142, that is encoded with or represents data pertaining to implement 126, such as information about its type, power requirements, date of creation, etc. Imager 14 of module 10 is positioned for optical communication with receptacle 132 and aligned to capture images of plug 134 when it is inserted into socket 132.

Module 10 may be triggered to capture an image of plug 134 in a variety of ways. As explained above, module 10 may be triggered and untriggered by host commands. Accordingly, base microcontroller 128 may be programmed or provided with software for transmitting the appropriate host commands to module 10 to trigger imager 14 and/or RFID unit 16. Module may also be programmed to detect the presence of plug 134 when it is presented or inserted into receptacle 132. Module 10 may also be programmed to routinely capture images of a trigger indicia 144 positioned or applied to the bottom of receptacle 132. When trigger indicia 144 is no longer visible, or the barcode information contained in trigger indicia 144 is no longer decipherable (presumably as a result of the insertion of plug 134 into receptacle 132), imager 14 may be triggered.

The captured image of plug 134 is processed by module microcontroller 12 to interpret the particular indicia provided on plug 134, such as barcode 140. Microcontroller 12 may also be programmed to detect the presence and arrangement of any legacy markings 146 applied to plug 134, such as dot patterns used by conventional electrosurgical scalpels to detect the insertion of particular scalpels. Module 10 may further be programmed to perform advanced signal processing of the image of plug 134 obtained by imager 14. For example, microcontroller 12 may programmed to recognize a predetermined shape or logo applied to plug 134, such as a custom symbol 142 or even trademark. Alternatively, module 10 may be programmed to determine whether the particular trademark of the manufacturer appears on implement 126.

Module 10 is configured to provide base microcontroller 128 with a message comprising a byte packet including predefined parameters that reflect the data that module 10 has been programmed to extract from the image of plug 134. For example, a byte packet may include parameters reflecting the type of processing being performed (e.g. barcode verses legacy decoding), the type of implement 126 that was identified (such as by catalog number), packet type (referencing the type of implement 126 that has been configured for interpretation), packet data (the information actually interpreted from the implement 126), and cyclic redundancy check (CRC). For example, an Aztec barcode is decoded and the data is sent in a packet back to base microcontroller 128 containing start and stop characters, the actual barcode data, and a software "exclusive or" of all the packet data. After successful decoding of image, the byte packet is sent by module 10 through interface 18 to base microcontroller 128. Module 10 may also provide a message reflecting whether receptacle 132 is empty or an unreadable indicia has been imaged.

Based on the data obtained by module 10, base unit 124 may determine whether the proper implement 126 has been connected, what level of power should be supplied to implement 126, and set the appropriate duration for the application of power to implement 126. If microcontroller 12 has been programmed to determine the presence or absence of a custom symbol, trademark, or logo, module 10 can provide the corresponding data to base microcontroller 128 to indicate whether a non-compatible or inferior implement has been inserted into receptacle 132.

Base microcontroller 128 may be programmed or supplied with host commands for operating module 10. For example, base microcontroller 128 may command module 10 to report on status, such as the type of processing being performed, the trigger method currently in use, or whether plug 134 is in receptacle 132. Base unit 124 may also direct imaging or re-imaging of plug 134 via a host trigger command. Other useful commands include commands requesting that module 10 resend the previous message, configuration commands controlling timeouts for imaging attempts, and commands directing module 10 to use a various decoding technique or switch between processing techniques.

Although RFID interrogation is optional for this embodiment of the present invention, base unit 124 may also be programmed to direct module 10 to perform RFID interrogation in addition to or in lieu of imaging of plugs 134. For example, base unit may trigger RFID unit 16 after initialization to read a medical ID badge presented by a nurse, medical technician, or physician before allowing any implement 126 to be energized by base unit 124. Module 10 may also be used to interrogate a patient ID badge or wristband, thereby allowing base unit 124 to confirm that the particular patient is and supposed to receive treatment using medical implement 126 by accessing local or remote databases containing the patient's electronic medical record. Module 10 may thus be used to enhance security at multiple levels beyond simply confirming that an appropriate implement 126 has been inserted into base unit 124.

Figure 6:
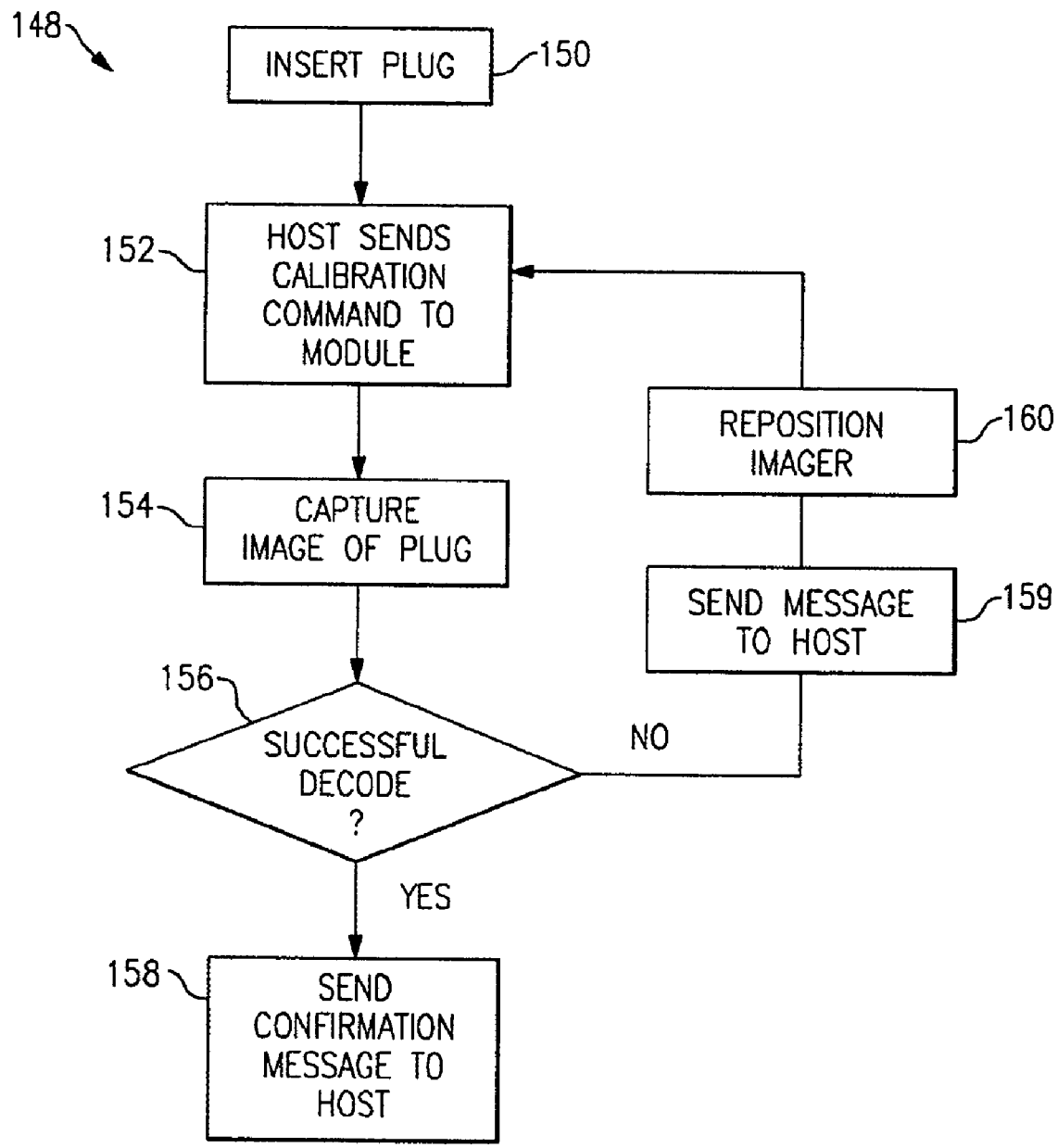
FIG. 6 is a flowchart of an instrument calibration process according to the present invention.

Referring to FIG. 6, the high-level calibration process 148 for device 122 implementing module 10 begins with by insertion 150 of plug 134 into receptacle 132 of base unit 124. Base unit 124 then sends a calibration command 152 to module 10 via interface 18. Upon receipt of the calibration command, module 10 attempts imaging 154 of plug 134. If imaging results in successful decoding 156 of the barcode 140, symbol 142 or legacy indicia 146, a message is sent 158 by module 10 to base unit 124 to confirm calibration. If no successful decoding occurs at step 156, a failure message is sent 159 to base unit 124 so that imager 12 may be repositioned 160 and the calibration process repeated until there is a successful confirmation at step 156. Calibration process 148 may also be conducted when trigger indicia 144 had been provided in receptacle 132 to verify that module 10 is capable of successfully decoding trigger indicia 144.

Figure 7:
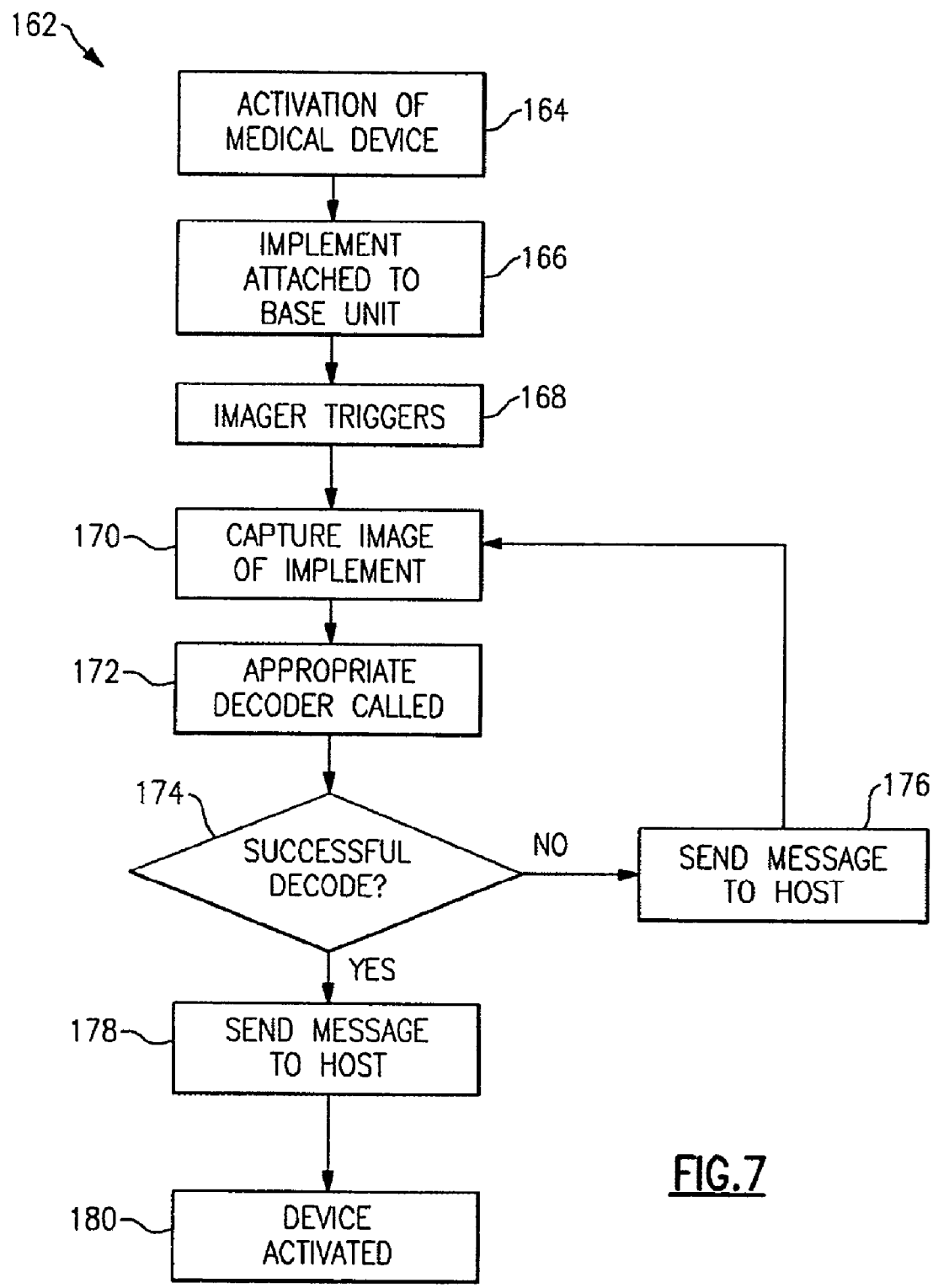
FIG. 7 is a flowchart of control processing according to the present invention.

Referring to FIG. 7, the implement identification process 162 of device 122 begins with activation 164, such as by interrogation of a medical worker's RFID tag or simply turning device 122 on. Implement 126 is then attached 166 to base unit 124 by inserting plug 134 into an available receptacle 132. Imager 12 of module 10 is then triggered to capture an image 168, via any of the methods described above, such as by the failure of imager 12 to successfully decode trigger image 144 at the bottom of receptacle 132. Imager 12 then captures an image 170 of plug 134 and microcontroller 12 calls the appropriate decoding technique or techniques 172. If the image cannot be decoded 174, a message is sent 176 to host device 122, and imaging may be repeated according to a predetermined timeout schedule (or at the command of device 122). If the image is successfully decoded at step 174, microcontroller 12 sends a message 178 to host microcontroller 128 reporting on the results of the decoding. If the information gleaned from decoding indicates that implement 126 is appropriate, host microcontroller 128 activates device 122 for operation 180, such as by automatically setting the appropriate level of energy and energizing implement 126. Information-gleaned by module 10, such as the particular type of implement 126, may be used by microcontroller 128 to a particular level of energy for a particular time. Alternatively, if the successful decoding of plug 134 reveals that an outdated implement 126 has been attached, microcontroller may disable device 122 and sent the appropriate alert to the user.

As module 10 is field programmable and host controllable, device 122 may be easily retrofit to include module 10, or easily upgraded once module 10 has been installed in the field. Along these lines, host microcontroller 128 may be easily programmed or supplied with software for controlling the operation of module 10, including optical imaging and/or RFID interrogation.

Figure 8:
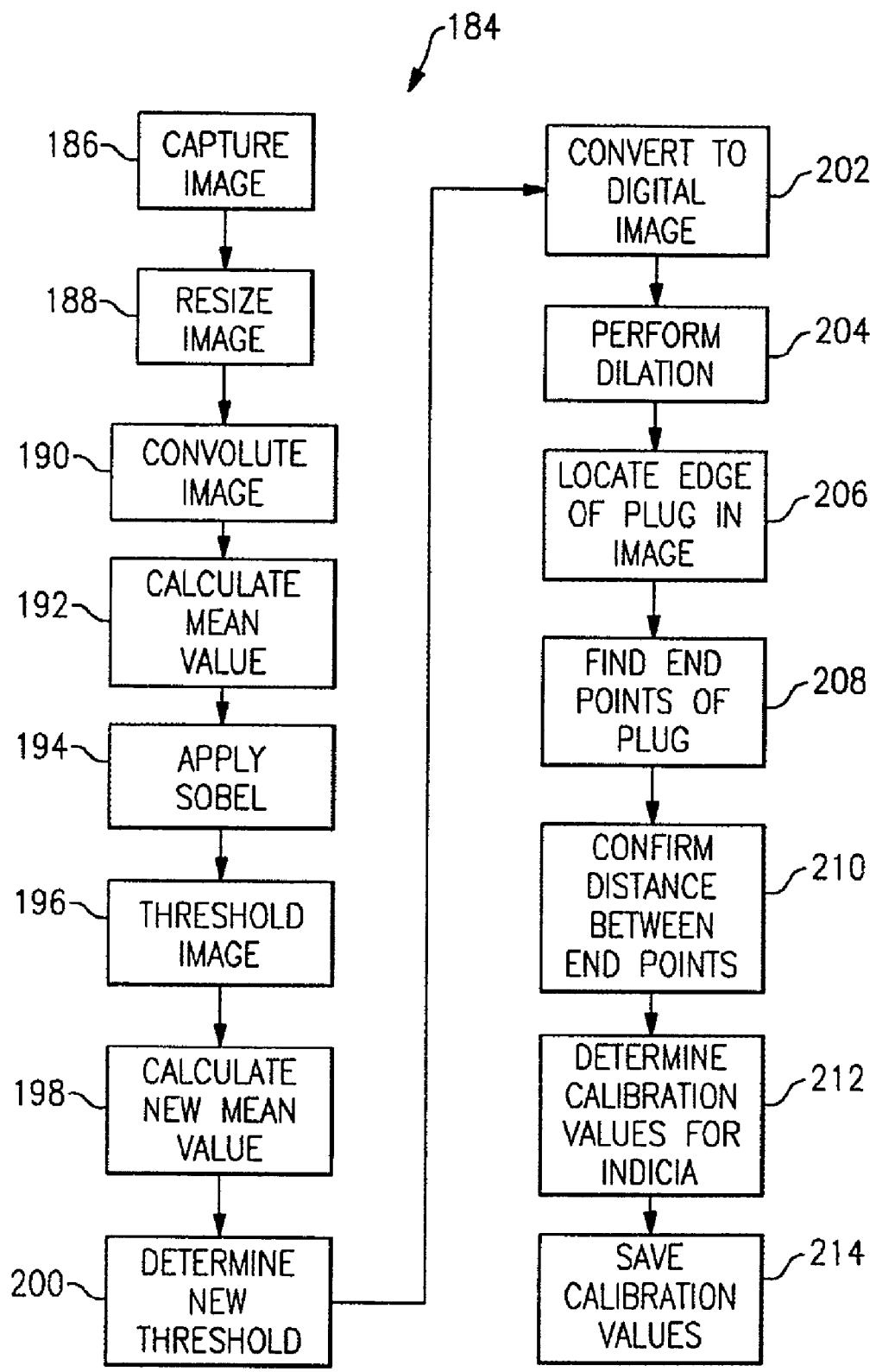
FIG. 8 is an illustration of a trigger image according to the present invention.

As mentioned above, module 10 should be calibrated for successful decoding of plug 134. There is seen in FIG. 8, a detailed plug calibration process. Plug calibration process 184 begins with the capturing of an image 184 of an inserted plug 134 having one or more of barcode 140, symbol 142 or legacy indicia 146. The image is then resized to one-third 188 (to simplify processing) and then blurred using a five by five convolution 190. A mean value for the image is calculated 192 to obtain a dynamic threshold that is used to improve image contrast. A Sobel edge detection algorithm is applied to the image 194, and the image is thresholded 196 to remove insignificant portions of the image. A new mean value is calculated 198 and a new threshold determined 200. The new threshold is used to convert the image from an 8 bit to digital 2 bit image 202. After digital conversion 202, a dilation operation is performed 204 to remove isolated points. The edge of plug 134 in the image is then located 206, and the vertical pixel line extending from the located edge is evaluated to find 108 its ends points, which should represent the corners of plug 134. The pixel distance between the end points may then be confirmed 210 to ensure that the captured image does in fact include plug 134. Once the pixel locations of plug 134 in the image is determined, calibration values representing the expected location of barcode 140, symbol 142 or legacy indicia 146 in the image can be determined 212, as the location of barcode 140, symbol 142 or legacy indicia 146 relative to the edges and corners of plug 134 is a known distance. The calibration values are then saved 214 for use during the implement identification process 162.

Figure 9A:
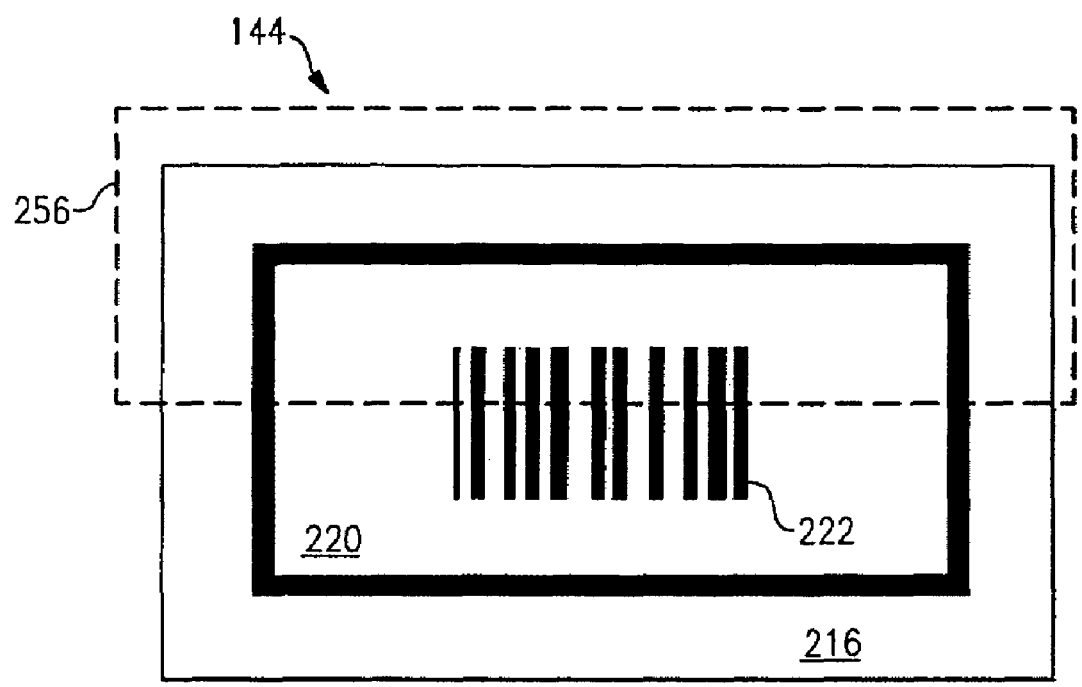
FIG. 9A, FIG. 9B, FIG. 10, and FIG. 11 are flowcharts of a trigger image calibration process according to the present.
Figure 9B:
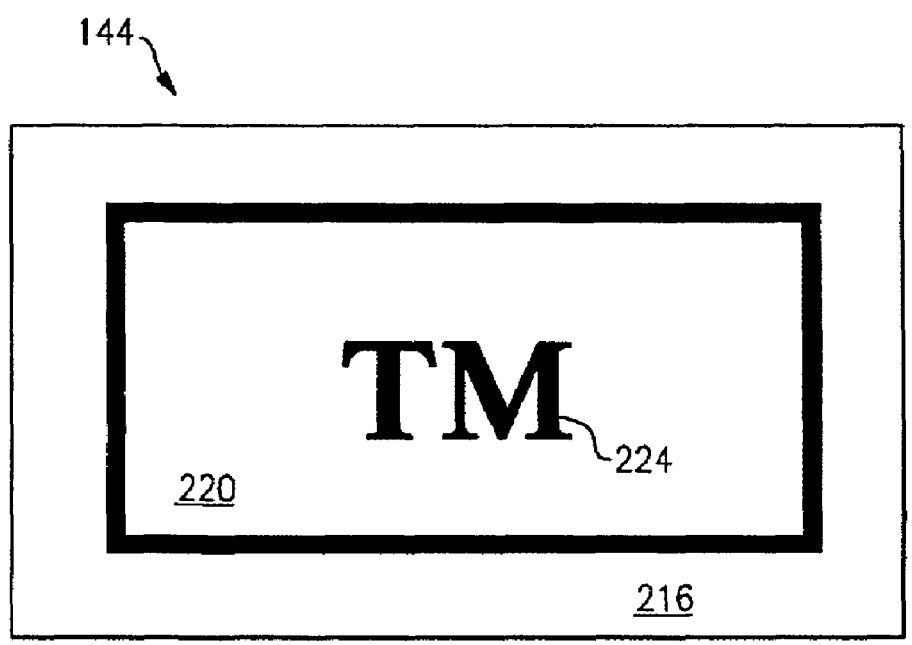
Figure 10:
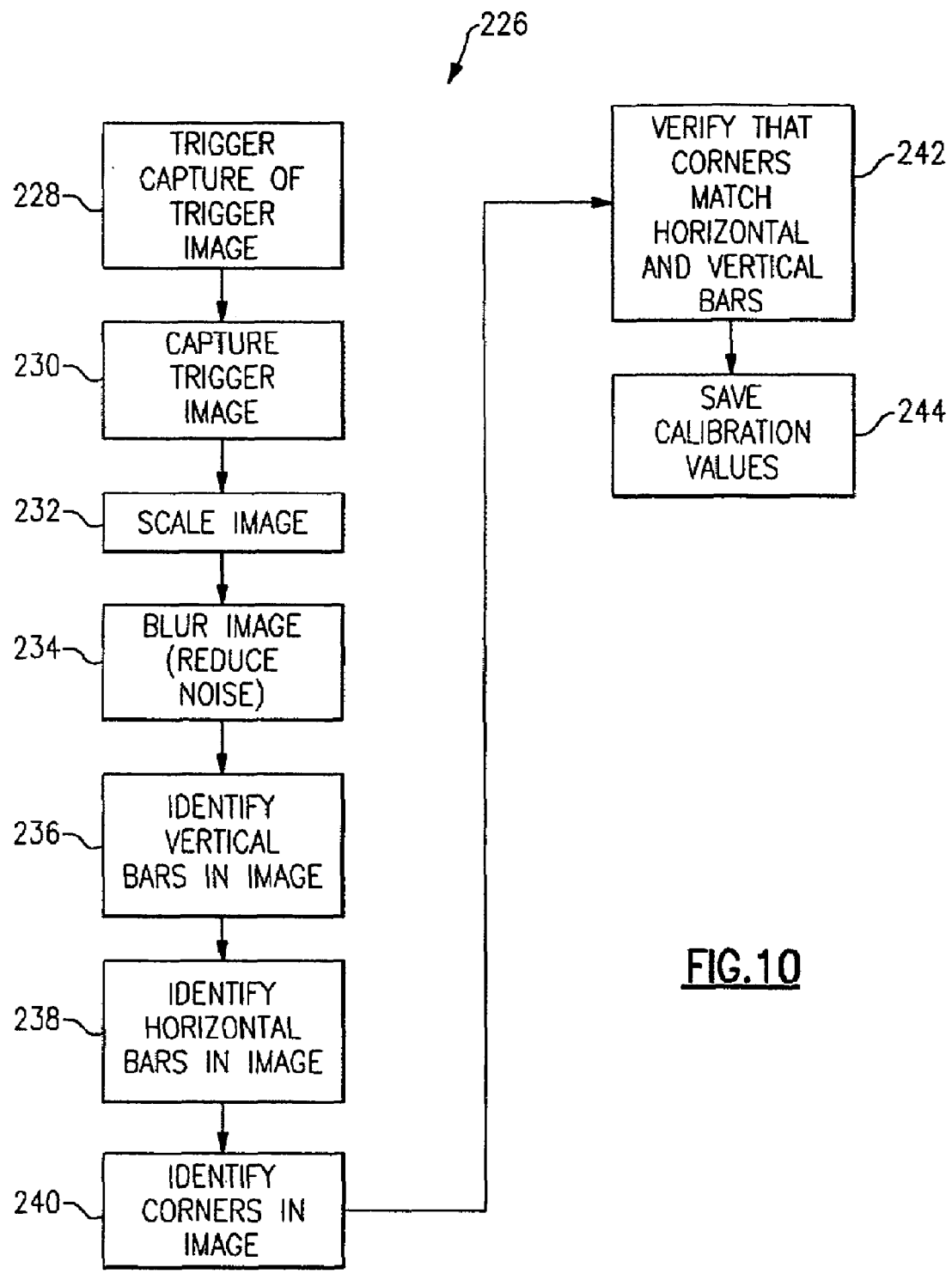

As discussed above, module 10 may be configured to be triggered when imager 14 can no longer decode or identify a trigger indicia 144 positioned at the bottom of receptacle 132. Referring to FIG. 9A, trigger indicia 144 may comprise a white background 216, a black box 218 inside white background 216 and defining an encircled white region 220. A a barcode 222 may be positioned within white region 220. As seen in FIG. 9B, a symbol 224 may instead by positioned within white region 220. Referring to FIG. 10, the trigger indicia calibration process 226 for automatically triggering imaging using trigger indicia 144 begins by initially triggering imager 228 to capture an image of trigger indicia 144. Next, the image is scaled 230 to reduce processing time and blurred 232 to reduce noise. The vertical bars of black box 218 are then identified 236. Identification 236 may occur by defining a horizontal row of a predefined number of pixels in height (such as three), summing the pixels in each pixel column, and then determining which pixel columns have the lowest energy levels (i.e., represent black). Once the lowest value pixel columns have been identified, the pixel distance between the lowest value pixel columns can be measured to confirm that the distance corresponds to the expected pixel distance between the vertical bars of an image of indicia 144. Similar steps can be performed to identify 238 the horizontal bars of indicia 144. The outside corners of black box 218 are then identified 240, and the locations of the horizontal and vertical bars are confirmed 242 by comparing to the locations of the corners. Finally, the pixel locations of the bars and corners are saved as calibration values 244. It should be recognized that any number of image processing algorithms and techniques may be used, provided they result in calibration values which can be used to readily locate trigger indicia 144 within a captured image.

Figure 11:
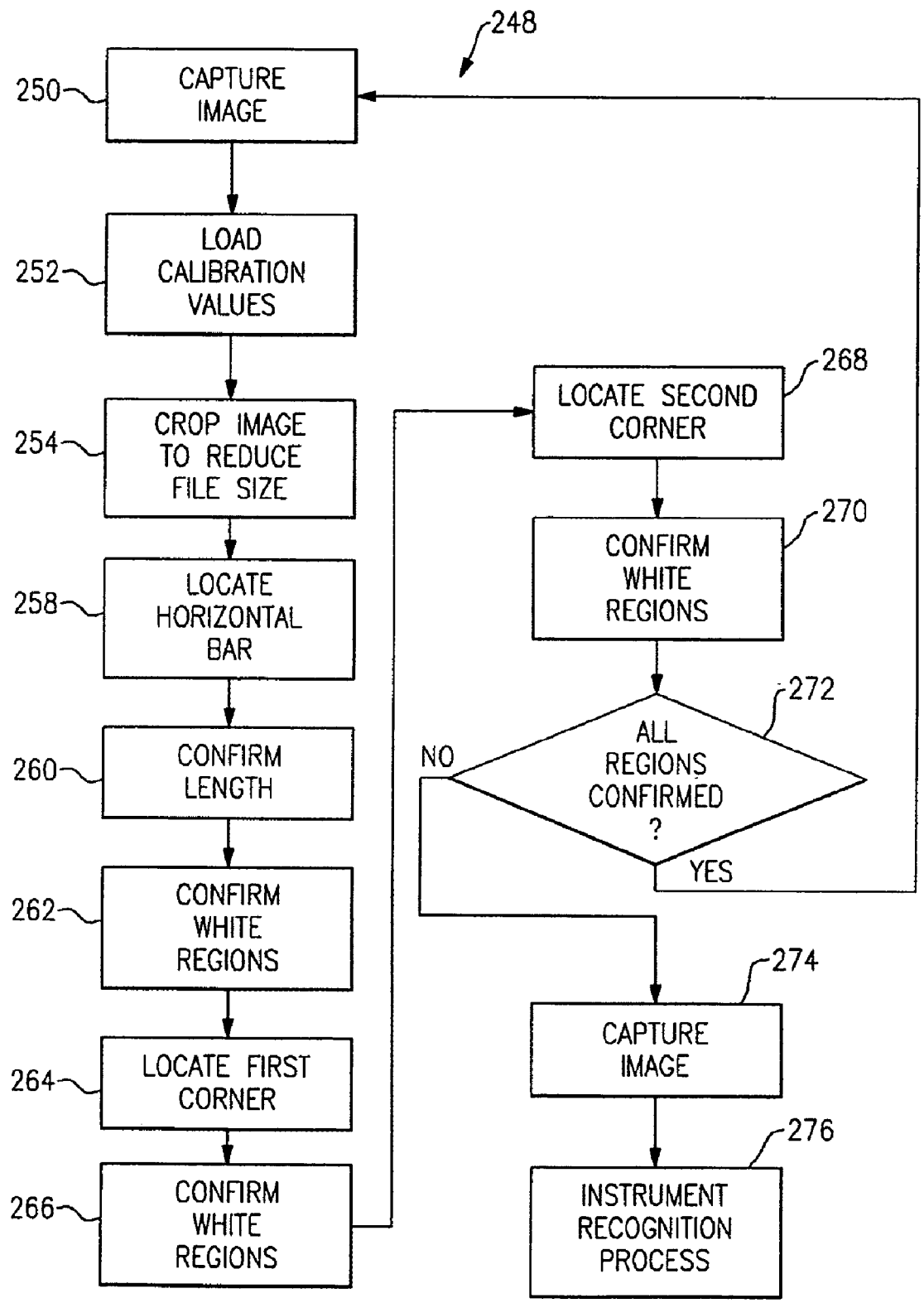

Referring to FIG. 11, the triggering process 248 using trigger indicia 144 comprises capturing an image 250 of receptacle 132 and loading the trigger indicia calibration values 252 (such as those saved at step 246 of calibration process 226). The image is then cropped 254 to include only an upper portion, as indicated by the dashed line 256 of FIG. 9A. The horizontal bar in the cropped image is then located 258 and its pixel length is confirmed 260 to be at least a predetermined length that is a percentage of the total length of the horizontal bar, to exclude any false readings. The regions above and below the horizontal bar are then checked to confirm 262 that they are in fact white background 216 and white region 220. A corner of box 218 is then located 264, and the surrounding white regions are confirmed 266. Finally, the opposing corner is located 268, and the surrounding white regions are confirmed 270. It should be recognized that any number of methods of confirming the presence of trigger indicia 144 may be employed, including additionally checking for the lower horizontal bar. If all appropriate regions are have been identified, as confirmed by check 272, process 240 determines that trigger indicia 144 is still visible, and therefore no implement 126 has been inserted. When the appropriate regions are not confirmed at step 272, an image is captured 274 and control is passed 276 to implement identification process 162 to identify what object has been interposed between imager 14 and trigger indicia 144. As explained above, trigger indicia 144 may be a barcode, custom code, symbol (such as a logo or trademark), or any other optically perceptible indicia that may be recognized by module 10.

What is claimed is:

1. A medical device, comprising:
    a base unit including a first microcontroller;
    an implement that may be selectively attached to said base unit;
    an optical imager positioned in said base unit and aligned to capture images of at least a portion of said implement when said implement is attached to said base unit; and
    a second microcontroller interconnected to said optical imager and said first microcontroller, wherein said second microcontroller is programmed to interpret commands sent by sent first microcontroller.

2. The apparatus of claim 1, wherein said second microcontroller is programmed to decode information within an image of said implement that is captured by said imager.

3. The apparatus of claim 2, wherein said second microcontroller is programmed to communicate a message to said first microcontroller about the information decoded from said image.

4. The apparatus of claim 3, wherein said second microcontroller triggers said optical imager when said implement is attached to said base unit.

5. The apparatus of claim 4, wherein said implement includes indicia that is decodable by said imager.

6. The apparatus of claim 5, wherein said indicia comprises a barcode.

7. The apparatus of claim 5, wherein said indicia comprises a symbol.

8. The method of operating a medical device comprising a base unit and at least one implement removably attached thereto, said method comprising the steps of:
    capturing an image of said implement when said implement is attached to said base unit; and;
    decoding information contained in said image;
    operating said device if said information indicates that said implement is acceptable for use with said device.

9. The method of claim 8, wherein said information is contained in indicia on said implement.

10. The method of claim 9, wherein said indicia comprises a barcode.

11. The method of claim 9, wherein said indicia comprises a dot pattern.

12. The method of claim 9, wherein said indicia comprises a symbol.

13. The method of claim 8, further comprising the step of interrogating an RFID tag prior to capturing an image of said implement.

14. A medical device, comprising:
    a base unit having a receptacle;
    an implement removably attached to said receptacle;
    an optical imager positioned to capture an image of said implement in said receptacle;
    a microcontroller interconnected to said optical imager, wherein said microcontroller is programmed to interpret the image of said implement.

15. The device of claim 14, further including an identifying indicia on said implement.

16. The device of claim 15, wherein said microcontroller is programmed to determine the type of said instrument based on said identifying indicia.

17. The method of claim 14, further including a trigger indicia positioned in said receptacle so that said trigger indicia is not visible to said imager when said implement is in said receptacle.

18. The method of claim 17, wherein said microcontroller is programmed to interpret the image of said implement when said trigger indicia is not visible.

19. The method of claim 18, wherein said trigger indicia comprises a logo.

* * * * *